United States Patent
Schmitt et al.

(10) Patent No.: US 10,123,861 B2
(45) Date of Patent: Nov. 13, 2018

(54) **BAG FOR PACKAGING DILUTED ANIMAL SEMEN SUITABLE FOR ARTIFICIAL INSEMINATION, IN PARTICULAR OF *PORCINE* SPECIES; AND SYSTEM COMPRISING SAME**

(71) Applicant: IMV TECHNOLOGIES, Saint Ouen sur Iton (FR)

(72) Inventors: Eric Schmitt, Villaines-la-Juhel (FR); Jean-Charles Gorges, Chenay (FR)

(73) Assignee: IMV TECHNOLOGIES, Saint Ouen sur Iton (FR)

( * ) Notice: Subject to any disclaimer, the term of this patent is extended or adjusted under 35 U.S.C. 154(b) by 8 days.

(21) Appl. No.: 15/524,281

(22) PCT Filed: Nov. 3, 2015

(86) PCT No.: PCT/FR2015/052950
§ 371 (c)(1),
(2) Date: Sep. 25, 2017

(87) PCT Pub. No.: WO2016/071618
PCT Pub. Date: May 12, 2016

(65) Prior Publication Data
US 2018/0021119 A1   Jan. 25, 2018

(30) Foreign Application Priority Data
Nov. 4, 2014   (FR) ..................................... 14 60647

(51) Int. Cl.
*A61B 17/06*   (2006.01)
*A61D 19/02*   (2006.01)
(Continued)

(52) U.S. Cl.
CPC .......... *A61D 19/022* (2013.01); *A01N 1/0215* (2013.01); *A01N 1/0263* (2013.01); *B65D 65/40* (2013.01); *B65D 75/30* (2013.01)

(58) Field of Classification Search
CPC ...... B65D 65/40; B65D 75/30; A61D 19/022; A01N 1/0215; A01N 1/0263
(Continued)

(56) References Cited

U.S. PATENT DOCUMENTS 2,648,463 A * 8/1953 Scherer .............. B65D 75/5855
156/292
5,391,163 A * 2/1995 Christine .................. A61J 1/10
604/403
(Continued)

FOREIGN PATENT DOCUMENTS

FR         2817242 A1    11/2000

OTHER PUBLICATIONS

Camilloto et al., Preservation of Sliced Ham Through Triclosan Active Film, Packaging Technology and Science, 22:471-477 (2009).

*Primary Examiner* — Luan K Bui
(74) *Attorney, Agent, or Firm* — Browdy and Neimark, P.L.L.C.

(57) ABSTRACT

The bag comprises two flexible sheets (11) attached to each other by a weld area delimiting a pouch having a predefined volume when said bag is filled, said pouch being designed to contain a dose (27) of said diluted animal semen having said predefined volume. The surface (30) of each of said flexible sheets (11) faces said pouch (14) which is part of a layer (35) of weldable thermoplastic material. For one or preferably for each of said sheets (11), said layer of weldable thermoplastic material (35) comprises triclosan; and the ratio between said predefined volume of said pouch and the sum of the areas of the surfaces (30) of said sheets (11) facing said pouch is between 0.3 ml/cm² and 0.5 ml/cm².

(Continued)

The system comprises such bags and an antibiotic-free dilution medium.

12 Claims, 3 Drawing Sheets

(51) Int. Cl.
    *A01N 1/02*         (2006.01)
    *B65D 65/40*      (2006.01)
    *B65D 75/30*      (2006.01)

(58) Field of Classification Search
    USPC ........... 206/438; 383/36, 121; 435/2; 600/35
    See application file for complete search history.

(56) References Cited

U.S. PATENT DOCUMENTS

| | | | |
|---|---|---|---|
| 5,735,401 A * | 4/1998 | Cassou | A61D 19/022 |
| | | | 206/469 |
| 6,149,579 A * | 11/2000 | Lee | A61D 19/022 |
| | | | 222/541.2 |
| 6,468,611 B1 * | 10/2002 | Haskin | A61B 50/00 |
| | | | 206/200 |
| 7,150,734 B2 * | 12/2006 | Lecointe | A61D 19/022 |
| | | | 604/408 |
| 2004/0126280 A1 | 7/2004 | Leaman, Jr. | |
| 2010/0150480 A1 * | 6/2010 | Lacointe | A61D 19/022 |
| | | | 383/121 |

* cited by examiner

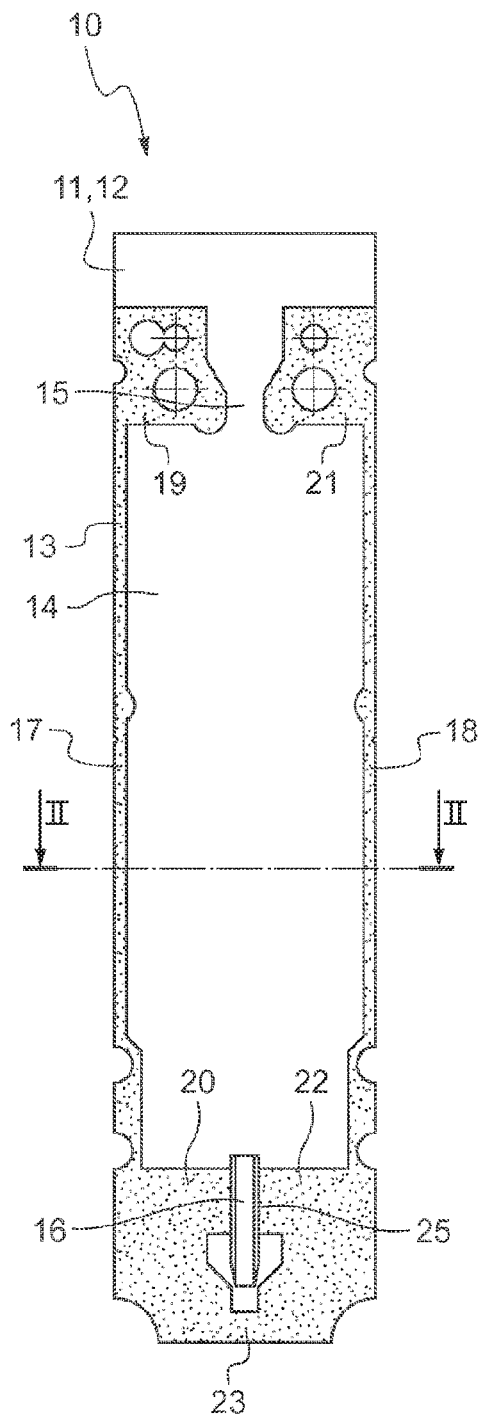
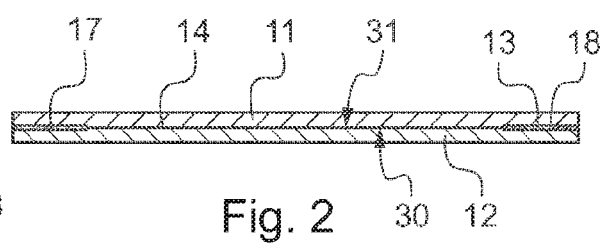
Fig. 1
Fig. 2

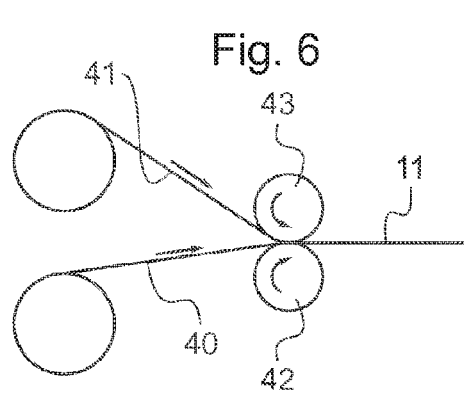
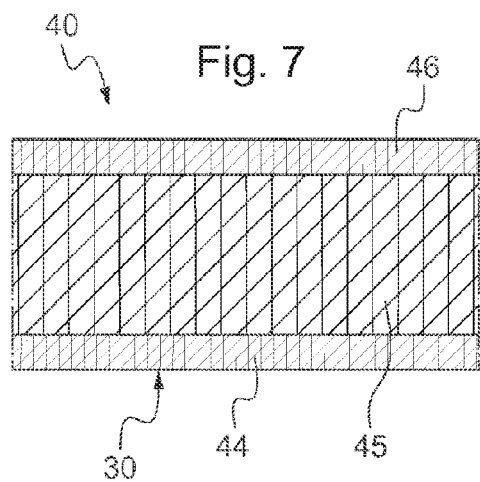
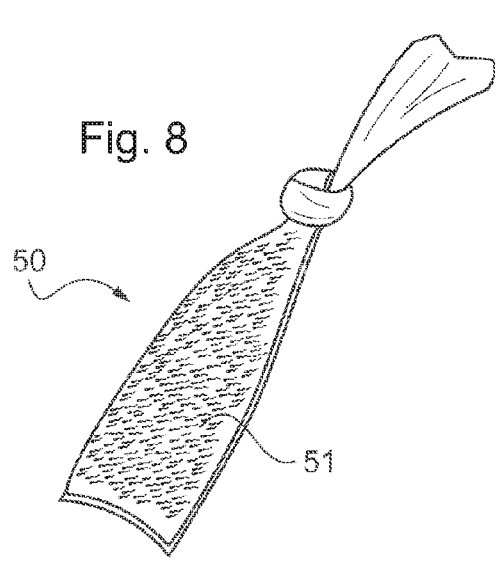
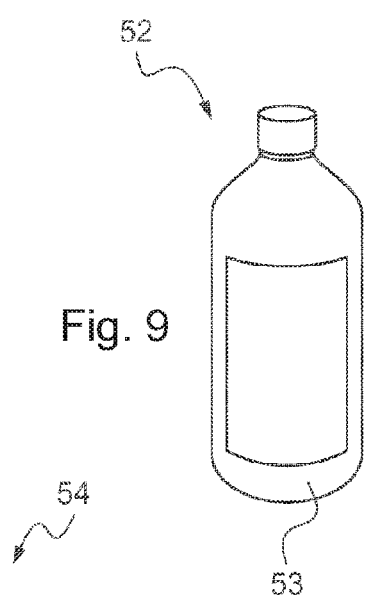
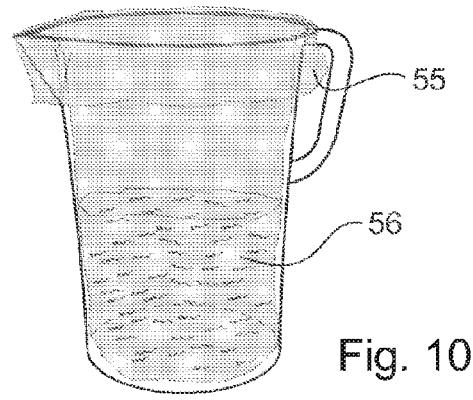

BAG FOR PACKAGING DILUTED ANIMAL SEMEN SUITABLE FOR ARTIFICIAL INSEMINATION, IN PARTICULAR OF *PORCINE* SPECIES; AND SYSTEM COMPRISING SAME

The invention generally relates to the preservation of diluted animal semen suitable for artificial insemination, in particular of porcine species.

It is known that for these species, between the collection of fresh semen and the insemination, the fresh semen is mixed with a dilution extender in order to obtain diluted semen then the diluted semen is packaged in individual doses each having a predetermined volume suitable for performing an artificial insemination, each dose being packaged in a receptacle in which it will be preserved until the artificial insemination is performed.

To package the individual doses of diluted semen, bags are already known, in particular from European patent application EP 0 605 406, from PCT application WO 01/13818, from French patent application 2 813 784 or from French patent application 2 848 812, comprising two sheets of flexible thermoplastic material fastened to each other by a weld zone delimiting a pouch having a predetermined volume when the bag is filled, said pouch being provided to contain a dose of diluted animal semen having that predetermined volume.

In general, the sheets of flexible thermoplastic material are double-layered, with the inside layer (layer having a surface facing the other sheet and facing the pouch) being of weldable thermoplastic material to enable the weld zone to be produced, and with the outside layer being in general gas-tight and having a higher melting point than that of the weldable thermoplastic material forming the inside layer.

The weld zone in general delimits, in addition to the pouch, a pipe by which the pouch is filled with diluted animal semen and a pipe serving to link the bag to an artificial insemination probe to transfer the dose packaged in the bag to the animal.

To preserve the quality of the semen during storage time, it is known to provide nutrients in the extender medium as well as antibacterial agents, in particular antibiotics.

The invention is directed to eliminating or in any case greatly reducing the use of antibiotics for the preservation of diluted animal semen.

To that end the invention provides a bag for packaging diluted animal semen suitable for artificial insemination, in particular of porcine species, comprising two flexible sheets fastened to each other by a weld zone delimiting a pouch having a predetermined volume when said bag is filled, said pouch being provided to contain a dose of said diluted animal semen having said predetermined volume, each said flexible sheet having its surface facing said pouch forming part of a layer of weldable thermoplastic material; characterized in that, for one or preferably for each said sheet, said layer of weldable thermoplastic material comprises triclosan; and the ratio between said predetermined volume of said pouch and the sum of the surface areas of the surfaces of said sheets facing said pouch is comprised between 0.3 ml/cm² and 0.5 ml/cm².

It is known that triclosan is $C_{12}H_7Cl_3O_2$ of which the formula is the following:

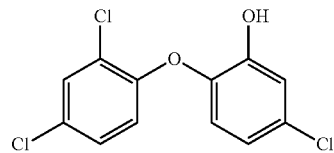 [SMILES: Oc1cc(Cl)ccc1Oc1ccc(Cl)cc1Cl]

and that it is identified by the number CAS 3380-34-5.

It is also known that triclosan is a biocidal substance able to be incorporated in plastic materials in order for them in turn to have biocidal properties, and that in principle triclosan is also considered as a spermicidal agent (see for example PCT application WO 00/72839).

Although this is surprising, the work carried out by the applicant has enabled it to be found that it is possible, in particular as disclosed below, to provide the layer of weldable thermoplastic material with a quantity of triclosan sufficiently large for the dose of diluted semen contained in the bag to remain bacteriostatic and sufficiently small so as not to be unfavorable to the motility of spermatozoids contained in the dose.

The invention is based on the observation that in a bag for preserving diluted semen, the surface area of the contact zone between the dose of diluted semen and the sheets of the bag is particularly high in relation to the volume which the pouch can contain.

Based on this observation, the question was posed as to whether the effect of the triclosan of the sheet or sheets on the diluted semen could occur not by release of the triclosan from the sheets into the semen but essentially by the effect of contact, given the extent of the aforementioned surface area whereby each part of the diluted semen contained in the bag is relatively close to the surfaces of the sheets facing the pouch.

In other words, the question was posed as to whether a surface effect (and not a volume effect) would suffice to obtain the bacteriostatic effect enabling the preservation of the dose of diluted semen.

This question was posed on the assumption that if the triclosan is not released into the diluted semen (or at the very least is released in a very small quantity), the effect of the triclosan on the spermatozoa will be minimal, and thus not unfavorable to their motility, and that the semen will therefore keep its fertilizing qualities.

The work conducted by the applicant has enabled it to be shown that if an appropriate quantity of triclosan was introduced into the layer of weldable thermoplastic material of the sheet or sheets of the bag, in particular as described below, it is indeed possible to obtain the bacteriostatic effect required for the preservation of the diluted semen without releasing triclosan (or at the very least releasing a very small quantity) into the dose contained in the bag, and that the spermatozoa indeed have a motility which still provides good performance further to their stay in the bag.

In the bag according to the invention, the range of values of the ratio between the volume of the pouch when it is filled and the surface area of the surfaces of the sheet or sheets facing the pouch has been selected as implementing the aforementioned combined technical effects in a particularly effective manner.

It will be noted that by virtue of the bag according to the invention, in the system formed by the dilution extender and by the bags for packaging, the effect of keeping the dose of diluted semen in bacteriostatic conditions is no longer required to be procured by the dilution extender, which makes it possible to eliminate or in any case to greatly reduce the antibiotics conventionally provided in the dilution extender.

It will also be noted that in the absence of release of triclosan into the dose of diluted semen contained in the bag, or in any case the virtual absence of release of triclosan into the diluted semen, the animal does not receive, or only receives a tiny quantity, of biocidal substance at the time of the artificial insemination.

According to advantageous features:
said predetermined volume of said pouch is comprised between 50 ml and 100 ml;
said layer of weldable thermoplastic material comprises between 1 mg/m$^2$ and 40 mg/m$^2$ of triclosan;
said layer of weldable thermoplastic material comprises between 10 mg/m$^2$ and 40 mg/m$^2$ of triclosan;
said layer of weldable thermoplastic material comprises several under-layers made of different grades of said weldable thermoplastic material, one or preferably each said flexible sheet having its surface facing said pouch forming part of the innermost sub-layer, only the innermost sub-layer comprising triclosan.
in the innermost sub-layer there is between 0.0075% and 0.3% by weight of triclosan;
said innermost sub-layer represents between 12% and 18% by weight of the layer of weldable thermoplastic material;
one or preferably each said flexible sheet comprises, in addition to said layer of weldable thermoplastic material, at least one other layer of material that is distinct from said weldable thermoplastic material, covering said layer of weldable thermoplastic material on the opposite side from said pouch, only said layer of weldable thermoplastic material comprising triclosan;
said other layer of material that is distinct from said weldable thermoplastic material is an outside layer made from a thermoplastic material;
said weldable thermoplastic material is polyethylene (PE) and said thermoplastic material of the outside layer is polyester (PET); and/or
said layer of weldable thermoplastic material has a thickness comprised between 20 μm and 110 μm.

According to a second aspect, the invention is also is directed to a system for packaging diluted animal semen in bags, suitable for artificial insemination, in particular for porcine species, comprising a dilution extender of fresh semen to give diluted semen and bags to fill with said diluted semen; characterized in that said bags are such as disclosed above and said dilution extender is without antibiotic.

The disclosure of the invention will now be continued with the detailed description of embodiments, given below by way of illustrative and non-limiting example, with reference to the accompanying drawings, in which:

FIG. 1 is a plan view of a bag according to the invention in the flat state, that is to say not filled;

FIG. 2 is the section view on II-II of FIG. 1;

FIG. 6 is a diagrammatic view showing a step of manufacturing a sheet of thermoplastic material with which the bag is made;

FIG. 7 is a cross-section view of one of the films shown in FIG. 6;

FIG. 8 shows a collecting bag containing fresh animal semen;

FIG. 9 shows a bottle containing a dilution extender to mix with the fresh animal semen to give diluted animal semen; and FIG. 10 shows a jug covered with a protective bag containing diluted animal semen obtained by mixing fresh animal semen from the bag of FIG. 8 and dilution extender from the bottle of FIG. 9.

Figure 3:
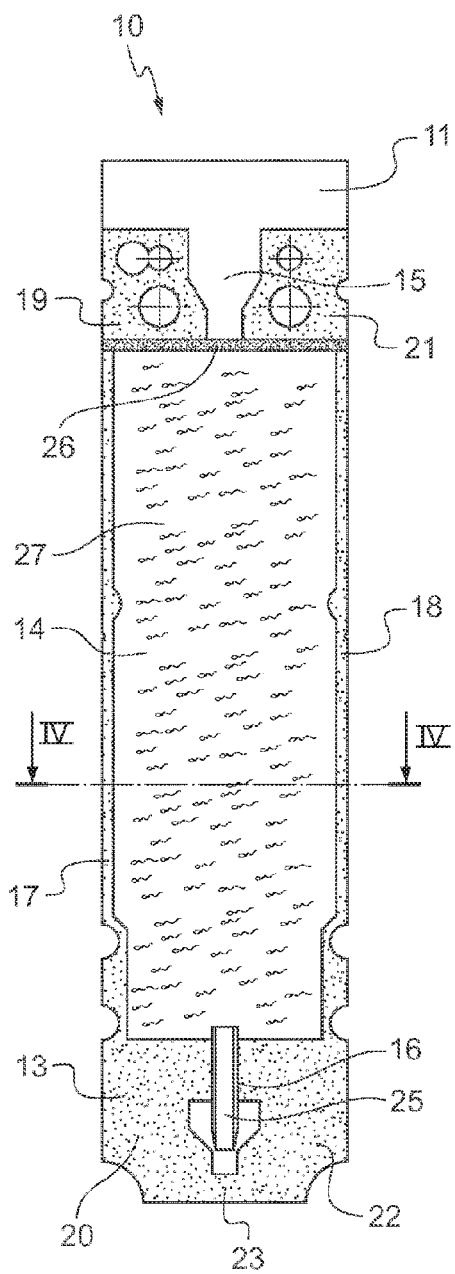
FIGS. 3 and 4 are similar views to FIGS. 1 and 2, but with the bag filled with a dose of diluted semen.

The bag 10 illustrated in FIG. 1 comprises two sheets 11 and 12 of flexible thermoplastic material fastened to each other by a weld zone 13 delimiting a pouch 14, a filling pipe 15 and an emptying pipe 16.

The weld zone 13 comprises two lateral portions 17 and 18, four end portions 19, 20, 21 and 22 as well as a bridging member 23.

The lateral portions 17 and 18 extend parallel to each other and spaced away from each other The lateral portion 17 is connected at one of its ends to the end portion 19 whereas it is connected at the other end to the end portion 20.

The lateral portion 18 is connected at one of its ends to the end portion 21 whereas it is connected at the other end to the end portion 22.

The bridging member 23 extends between the end portion 20 and the end portion 22.

The filling pipe 15 is located between the end portion 19 and the end portion 21.

The emptying pipe 16 is located between the end portion 20 and the end portion 22 and is closed, at the remote opposite from the pouch 14, by the bridging member 23.

Here, the lateral portions 17 and 18 are relatively narrow whereas the end portions 19, 20, 21 and 22 are relatively wide.

Here, each lateral portion 17 and 18 is situated between the pouch 14 and a respective edge of the bag 10.

In the flat state of the bag 10 shown in FIGS. 1 and 2, the pouch 14 is empty, the sheets 11 and 12 being against each other.

The pouch 14 has a generally rectangular contour of which the long sides are delimited by the lateral portions 17 and 18 and the short sides by the end portions 19, 21 and 20, 22.

The filling pipe 15 issues at one end inside the pouch 14 and at the other end outside the pouch 14.

The emptying pipe 16 issues at one end inside the pouch 14 and is closed at the other end by the bridging member 23.

In addition to the sheets 11 and 12 fastened together by the weld zone 13, the bag 10 here comprises a canula 25 disposed in the emptying pipe 16.

To fill the bag 10, and more specifically the pouch 14 thereof, the diluted semen is introduced by the filling pipe 15.

In practice, a tip is used which is inserted into the filling pipe 15 to begin to give volume to the bag.

Once the bag 10, and more specifically the pouch 14, has thus been filled with the dose 27 (FIGS. 3 and 4) of diluted semen which has the predetermined volume for which the pouch 14 was configured, the filling pipe 15 is obturated by virtue of a weld bead 26 (FIG. 3).

The packaging of the dose 27 of diluted semen is then terminated.

To perform an artificial insemination with the dose 27 of diluted semen contained in the bag 10, the canula 25 is freed, for example by striking the bridging member 23 with the opposite end of the canula from the pouch 14, the opposite end of the canula 25 to the pouch 14 thus becomes accessible and connection of an artificial insemination probe is made thereto.

For more detail on the bag 10, reference may be made to French patent application 2 813 784.

The bag 10 illustrated in FIGS. 1 to 4 is provided to contain a dose 27 of diluted semen of which the volume is 70 ml.

When the bag 10 is in the flat state (FIGS. 1 and 2), the width of the pouch 14 (distance between the lateral portions 17 and 18) is 5.5 cm and the distance between the end portions 19, 21 and 20, 22 is 17.3 cm.

Thus, the surface area of the surface 30 of sheet 11 facing the pouch 14 is 95 cm$^2$.

Similarly, the surface area of the surface 31 of sheet 12 facing the pouch 14 is 95 cm$^2$.

Figure 4:
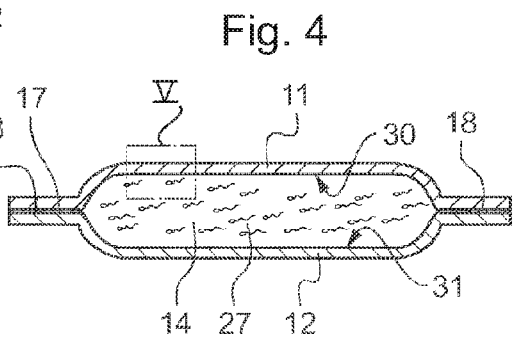

Naturally, this surface area remains the same when the bag is in the filled state shown in FIGS. 3 and 4.

Thus, the sum of the surface areas of sheets 11 and 12 facing the pouch 14 is 95 cm$^2$+95 cm$^2$ which is to say 190 cm$^2$.

The ratio between the volume which is provided that contains the pouch 14 and the sum of the surface areas of the sheets 11 and 12 facing the pouch 14 is thus 70 ml/190 cm$^2$ which is to say 0.37 ml/cm$^2$.

Figure 5:
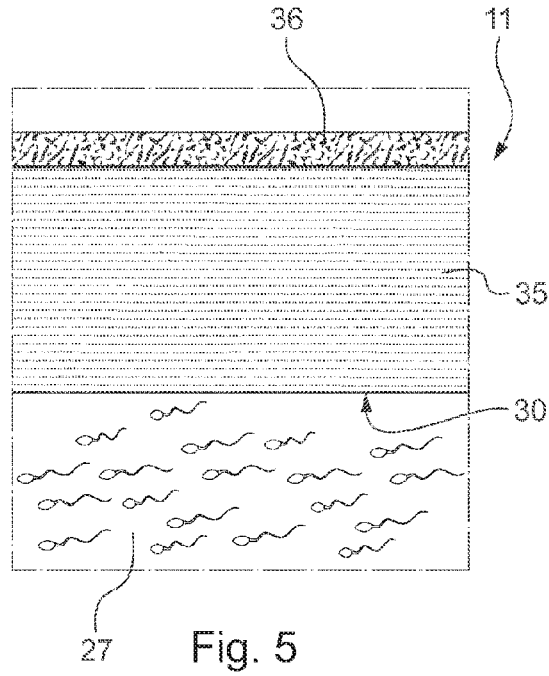
FIG. 5 is an enlargement of detail V of FIG. 4.

A description will now be given of the arrangement of the sheet 11, with reference to FIG. 5.

It is understood that this description also applies to the sheet 12, which is identical.

The sheet 11 is made from two materials: it comprises an inside layer 35 and an outside layer 36. The inside layer 35 is of a first thermoplastic material and the outside layer 36 is of a second thermoplastic material different from the first material.

The surface 30 facing the pouch 14 forms part of the inside layer 35.

Here, the first thermoplastic material with which the inside layer 35 is made is polyethylene (PE) and the thermoplastic material with which the outside layer 36 is made is polyester (PET).

It is known that polyethylene (PE) is a plastic material that can be welded relatively easily, the temperature of its melting point being relatively low and in any case lower than the temperature of the melting point of polyester (PET).

Thus, the weld zone 13 may be produced between the sheets 11 and 12 with electrodes brought to a temperature higher than the melting point of the polyethylene (PE) and lower than the melting point of the polyester (PET), such that there is no melting of the outside layer 36 of the sheets 11 and 12 when the weld zone 13 is formed. The outside faces of the sheets 11 and 12 therefore maintain their initial smooth appearance.

It is also known that polyester (PET) provides good gas-tightness, contrary to polyethylene (PE), such that the sheets 11 and 12 are not only liquid-tight but also gas-tight.

A description will now be given of how the sheet 11 is manufactured, with reference to FIG. 6.

It is to be understood that the description given below for the manufacture of sheet 11 also applies to the sheet 12 which is identical.

Sheet 11 is manufactured by superposition of two films 40 and 41 each from a spool on which it is stored, the superposed films being compressed, with heating, by a pair of rollers 42 and 43 between which the superposed films pass. The films 40 and 41 are thus co-laminated. In sheet 11, the inside layer 35 comes from the film 40 and the outside layer 36 comes from the film 41.

The film 41 is prepared by simple extrusion of a single grade of polyester (PET).

The film 40 is prepared by co-extrusion of three different grades of polyethylene (PE), such that film 40 has three superposed sub-layers 44, 45 and 46, as shown in FIG. 7.

Sub-layer 44 is the innermost sub-layer Therefore, the surface 30 of sheet 11 forms part of sub-layer 44.

The sub-layer 46 is the outermost sub-layer, which is therefore covered with the outside layer 36.

Sub-layer 45 is an intermediate sub-layer between sub-layer 44 and sub-layer 46.

Sub-layer 46 is provided for the binding between films 40 and 41. To form sub-layer 46, pellets of a grade of a polyethylene (PE) appropriate for performing the binding with the polyester (PET) are used.

Sub-layer 45 is provided to give certain mechanical characteristics to sheet 11. To form sub-layer 45, pellets of a grade of polyethylene (PE) appropriate to provide these mechanical characteristics are used.

The innermost sub-layer 44 is provided to be weldable with the corresponding sub-layer of the other sheet of the bag 10, in order for the weld zone 13 to be formed. Sub-layer 44 is furthermore provided to interact with the dose of diluted semen 27 via the surface facing the pouch 14, that is to say surface 30.

To form sub-layer 44, pellets of polyethylene of an appropriate grade for welding are mixed with pellets of an association of polyethylene and triclosan that has 15% by weight of triclosan.

The proportions of the mixture of pellets are 99% by weight of polyethylene pellets and 1% by weight of pellets of the association of polyethylene and triclosan.

The mixed material obtained thus contains 1% by weight of pellets of the association of polyethylene and triclosan. Therefore, the mixed material obtained contains 0.15% by weight of triclosan. The sub-layer 44 therefore contains 0.15% by weight of triclosan.

As indicated above, films 40 and 41 are superposed and compressed, with heating, by a pair of rollers 42 and 43 between which they pass to give the sheet 11.

It will be noted that in sheet 11, it is relatively easy to observe the existence of the inside layer 35 and the outside layer 36, but that due to the passage between the rollers 42 and 43, it is difficult to distinguish the sub-layers 44, 45 and 46 in the inside layer 35, which are nevertheless present.

In sheet 11, the sub-layer 44 represents 13% of the total weight of the sheet 11. Therefore, in sheet 11 there are 0.15%×13%, i.e. 0.02%, or in other words 20 mg of triclosan for 100 g of sheet 11.

As sheet 11 has a density of 92 g/m$^2$, there are 18 mg of triclosan per m$^2$ of film.

A description will now be given, with reference to FIGS. 8 to 10, of how the diluted semen provided to be packaged in the bag 10 is prepared.

FIG. 8 shows a collecting bag 50 containing fresh animal semen 51, here boar semen.

FIG. 9 shows a bottle 52 containing a dilution extender 53 to mix with fresh animal semen such as the semen 51 to give diluted animal semen such as that of the dose 27. The dilution extender 53 is without antibiotic.

FIG. 10 shows a jug 54 covered by a protective bag 55.

The assembly formed by the jug 54 covered with the bag 55 contains diluted animal semen 56 obtained by mixing fresh animal semen 51 from the collecting bag 50 with the dilution extender 53 from the bottle 52.

The diluted semen 56 is provided to be subdivided into individual doses 27 each filling a bag 10.

A description will now be given of an example of results obtained with the bag 10 for the preservation of diluted semen.

EXAMPLE 1

In addition to the bag 10 (hereinafter "bag A") a bag (hereinafter "bag B") is used that is similar to bag 10 but of which the sheets such as 11 and 12 are conventional, that is to say without triclosan.

On the basis of a same collected specimen of fresh semen 51, a preparation is made extemporaneously within the hour and in any case at latest within twenty-four hours, of diluted semen 56 diluted with the dilution extender without antibiotic 53 (hereinafter "diluted semen A") and a preparation is also made of semen diluted with a conventional dilution extender containing an antibiotic (hereinafter "diluted semen B").

The dilution is made such that the diluted semen A and the diluted semen B have a concentration of 35 million spermatozoa per ml.

A bacterial count made on samples then taken has enabled verification that diluted semen A and diluted semen B initially have a similar bacterial content.

A bag A is next filled with a dose of diluted semen A, a bag B with a dose of diluted semen B and a bag B with a dose of diluted semen A.

Next the bags are left to rest for six days in the usual preservation conditions, that is to say 17° C. in horizontal position.

The diluted semen of each bag is next analyzed.

A bacterial count is made and an evaluation is made of the motility of the spermatozoa.

The same is performed with five other collected specimens of fresh boar semen.

The tables below give the average results obtained for the six collected specimens.

As regards the bacterial count, the results are the following:

|  | Bacterial count (CFU/ml) |
| --- | --- |
| bag B diluted semen A | $5 \cdot 10^4$ |
| bag A diluted semen A | $3 \cdot 10^4$ |
| bag B diluted semen B | $1 \cdot 10^4$ |

The bacterial count was carried out by collecting samples then culture of the collected samples in Petri dishes containing Trytone Soya Agar (TSA) growth medium for forty-eight hours at 30° C. Half the sample are cultured in aerobic conditions and the other half in anaerobic conditions. The results obtained are averaged, these results being expressed in colony forming units (CFUs) per ml.

As regards the motility of the spermatozoa, the results are the following:

|  | Motility (%) |
| --- | --- |
| bag B diluted semen A | 65 |
| bag A diluted semen A | 61 |

The analysis of motility is carried out by a device for computer assisted sperm analysis commercialized by the applicant under the name CASA (Computer Assisted Sperm Analysis).

This is the analysis of images determining the percentage of mobile spermatozoa relative to all the spermatozoa.

A description will now be given of two other examples of results obtained with bags similar to the bag 10 but comprising a different amount of triclosan.

EXAMPLE 2

This is proceeded with as for Example 1 but with bags of which the sub-layer such as 44 of the sheets such as 11 and 12 is formed with a mixture of pellets of which the proportions are not 99% by weight for the polyethylene pellets and 1% by weight for the pellets of the association of polyethylene and triclosan, but 99.5% by weight of the polyethylene pellets and 0.5% by weight of the pellets of the association of polyethylene and triclosan.

The sheets of bag A in this example contain 10 mg of triclosan for 100 g of sheet, that is to say approximately 9 mg of triclosan per m² of sheet; and the innermost sub-layer 44 contains 0.075% by weight of triclosan.

As regards the bacterial count, the results obtained are the following:

|  | Bacterial count (CFU/ml) |
| --- | --- |
| bag B diluted semen A | $5 \times 10^4$ |
| bag A diluted semen A | $0.7 \times 10^4$ |
| bag B diluted semen B | $1 \times 10^4$ |

As regards motility, the results are the following:

|  | Motility (%) |
| --- | --- |
| bag B diluted semen A | 65 |
| bag A diluted semen A | 65 |

EXAMPLE 3

This is proceeded with as for Example 1 but with bags of which the sub-layer such as 44 of the sheets such as 11 and 12 is formed with a mixture of pellets of which the proportions are not 99% by weight for the polyethylene pellets and 1% by weight for the pellets of the association of polyethylene and triclosan, but 98.5% by weight of the polyethylene pellets and 1.5% by weight of the pellets of the association of polyethylene and triclosan.

The sheets of bag A in this example contain 29 mg of triclosan for 100 g of sheet, that is to say approximately 27 mg of triclosan per m² of sheet; and the innermost sub-layer 44 contains 0.225% by weight of triclosan.

As regards the bacterial count, the results obtained are the following:

|  | Bacterial count (CFU/ml) |
| --- | --- |
| bag B diluted semen A | $5 \cdot 10^4$ |

-continued

| | Bacterial count (CFU/ml) |
|---|---|
| bag A diluted semen A | $0.04 \cdot 10^4$ |
| bag B diluted semen B | $1 \cdot 10^4$ |

As regards motility, the results obtained are the following:

| | Motility (%) |
|---|---|
| bag B diluted semen A | 65 |
| bag A diluted semen A | 65 |

Amount of Triclosan Released

A description will now be given of the trials with the bag of Example 3 to determine the amount of triclosan released into the dose of diluted semen such as 27 contained in the pouch such as 14 of that bag.

To simplify the trials, it was not a dose of diluted semen which was preserved in the bag but only dilution extender.

In this case, the dilution extender 53 (hereinafter "extender A") and a conventional dilution extender containing an antibiotic (hereinafter "extender B") were used.

One bag of Example 3 is filled with a dose of extender A and one bag of Example 3 with a dose of extender B.

Next the bags are left to rest for five days in the usual preservation conditions, that is to say 17° C. in horizontal position.

Next, the extender contained in each bag is analyzed, in order to determine the concentration of triclosan.

This analysis is made by liquid chromatography tandem mass spectrometry (LC-MS-MS method).

Based on the concentrations obtained, the amount of triclosan released is determined in a full dose provided to be contained in the bag, that is to say 70 ml.

It will be noted that the weight of triclosan taken into account in the sheets such as 11 and 12 of the bag of Example 3 for calculating the proportion released is not the weight of triclosan in the entirety of these sheets, but only in the parts facing the pouch such as 14. Here, these parts weigh approximately 1.835 g (determined after cutting out and weighing). As there are 29 mg of triclosan for 100 g of sheet. The amount of triclosan contained in these parts is approximately 532 µg.

The results obtained are the following:

| | Amount of triclosan released into the dose | Proportion of triclosan released into the dose |
|---|---|---|
| Extender A | 2.7 µg | 0.5% |
| Extender B | 1.9 µg | 0.35% |

The results of the various analyses described above will now be commented upon.

In general, for these various analyses, the dispersion around the average values is low, such that the results given above can be considered as significant.

The results concerning the amount of triclosan released into the dilution extenders will now be commented upon.

It is found that the amounts released are tiny (here, around 1%).

The applicant considers that with the various existing dilution extenders, the amount released should remain tiny, for example less than 2% by weight.

The results concerning the bacterial count will now be commented upon.

It will be noted that for each sample, further to the preservation period, the population of bacteria is significantly lower for the bags according to the invention, that is to say the bags A containing the diluted semen A, than for the control bags, that is to say the bags B containing the diluted semen A.

It will also be noted that for each example, further to the preservation period, the population of bacteria is comparable for the bags according to the invention and for the conventional bags, that is to say that the bags B containing the diluted semen B, or even is lower for the bags according to the invention.

It may therefore be considered that the bags according to the invention have the capability to preserve diluted semen with an extender without antibiotic (semen A) in bacteriostatic conditions.

The results concerning the motility of the spermatozoa will now be commented upon.

It will be noted that further to the preservation period, the motility is comparable for the bags according to the invention (bags A) and the conventional bags (bags B).

It may thus be considered that the triclosan that the bags according to the invention contain do not perturb the motility of the spermatozoa.

In general, it was determined that the bag according to the invention provides good performance when the ratio between the volume of the pouch such as 14 and the sum of the surface areas of the surfaces such as 30 and 31 of the sheets such as 11 and 12 facing said pouch is comprised between 0.3 ml/cm² and 0.5 ml/cm².

Similarly, it has been determined that the bag according to the invention provides good performance when the volume of the pouch such as 14 is comprised between 50 ml and 100 ml.

It has also been determined that the bag according to the invention provides good performance when the innermost sub-layer such as 44 represents between 12% and 18% by weight of the inside layer such as 35 of weldable thermoplastic material.

In the illustrated example, the thickness of the inside layer such as 35 is of the order of 80 µm. It has also been determined that the bag according to the invention provides good performance when the thickness of the inside layer such as 35 is comprised between 20 µm and 110 µm.

It has also been determined that the bag according to the invention provides good performance when the inside layer such as 35 comprises between 1 mg/m² and 40 mg/m² of triclosan, preferably between 10 mg/m² and 40 mg/m².

It has moreover been determined that the bag according to the invention provides good performance when in the innermost sub-layer such as 44 there is between 0.0075% and 0.3% by weight of triclosan, preferably between 0.075% and 0.3% by weight triclosan.

It will now be described how the quantity of triclosan contained in the sheet 11 or the sheet 12 may be determined.

It will be noted that the determined quantity is expressed in weight per unit area of such a sheet (here in mg/m²).

A sample of sheet 11 or 12 is cut up at the location of the pouch 14 of the bag 10. This sample has a determined surface area, for example 1 cm².

The sample is then immersed in acetone and subjected to sonication for 2 h in order to extract the triclosan therefrom.

The concentration of triclosan in the solution obtained is next determined by liquid chromatography in the manner described above in relation to the amount of triclosan released.

This analysis (immersion in acetone with sonication then determination of the concentration of the solution obtained) with the same sample is repeated as many times as necessary until no more triclosan is detected in the solution obtained.

The amounts of triclosan determined at each analysis are then added together in order to obtain the total amount of triclosan initially present in the sample.

This amount is lastly expressed as a ratio in relation to the surface area of the sample.

It will be noted that the amount of triclosan in the inside layer 35 alone may be determined by eliminating the outside layer 36 beforehand, for example by erosion or delamination. However, here, as there is no triclosan in the outside layer 36, the amount of triclosan per unit area does not change.

Of course, it is possible to extract the triclosan from the sample with a solvent different from acetone, for example dichloromethane, with or without sonication; and to determine the concentration of the solution obtained by another method, for example high performance liquid chromatography (HPLC) coupled with a UV diode array detector DAD (HPLC-UV-DAD method).

In the illustrated examples, triclosan is provided only in the innermost sub-layer 44 of the inside layer 35, which is particularly economical. In variants not illustrated, there is triclosan elsewhere than in the innermost sub-layer, for example in the whole of the outside layer such as 35 or even in the outside layer such as 36; or only one of the sheets 11 and 12 comprises triclosan.

In variants not illustrated, the outside layer 36 of polyethylene (PET) is replaced by a layer of polyamide, by a layer of aluminum or by a layer of EVOH/Polypropylene; and rather than co-laminating films such as 40 and 41, the sheet 11 or 12 is manufactured entirely by co-extrusion.

In variants not illustrated, the arrangement of the bag is different, with for example the same pipe serving both for the filling and for the emptying; or else there is no canula for the emptying.

Numerous other variants are possible according to circumstances, and in this connection it is to be noted that the invention is not limited to the examples described and shown.

The invention claimed is:

1. A bag for packaging diluted animal semen suitable for artificial insemination, in particular of porcine species, comprising two flexible sheets (11, 12) fastened to each other by a weld zone (13) delimiting a pouch (14) having a predetermined volume when said bag (10) is filled, said pouch (14) being provided to contain a dose (27) of said diluted animal semen having said predetermined volume, each said flexible sheet (11, 12) having its surface (30, 31) facing said pouch (14) forming part of a layer (35) of weldable thermoplastic material; characterized in that, for one or preferably for each said sheet (11, 12), said layer of weldable thermoplastic material (35) comprises triclosan; and the ratio between said predetermined volume of said pouch (14) and the sum of the surface areas of the surfaces (30, 31) of said sheets (11,12) facing said pouch (14) is comprised between 0.3 ml/cm$^2$ and 0.5 ml/cm$^2$.

2. A bag according to claim 1, characterized in that said predetermined volume of said pouch (14) is comprised between 50 ml and 100 ml.

3. A bag according to claim 1, characterized in that said layer of weldable thermoplastic material (35) comprises between 1 mg/m$^2$ and 40 mg/m$^2$ of triclosan.

4. A bag according to claim 3, characterized in that said layer of weldable thermoplastic material comprises between 10 mg/m$^2$ and 40 mg/m$^2$ of triclosan.

5. A bag according to claim 1, characterized in that said layer of weldable thermoplastic material (35) comprises several under-layers (44, 45, 46) made of different grades of said weldable thermoplastic material, one or preferably each said flexible sheet (11, 12) having its surface (30, 31) facing said pouch (14) forming part of the innermost sub-layer (44), only the innermost sub-layer (44) comprising triclosan.

6. A bag according to claim 5, characterized in that in the innermost sub-layer (44) there is between 0.0075% and 0.3% by weight of triclosan.

7. A bag according to claim 5, characterized in that said innermost sub-layer (44) represents between 12% and 18% by weight of the layer (35) of weldable thermoplastic material.

8. A bag according to claim 1, characterized in that one or preferably each said flexible sheet (11, 12) comprises, in addition to said layer (35) of weldable thermoplastic material, at least one other layer (36) of material that is distinct from said weldable thermoplastic material, covering said layer (35) of weldable thermoplastic material on the opposite side from said pouch (14), only said layer (35) of weldable thermoplastic material comprising triclosan.

9. A bag according to claim 8, characterized in that said other layer (36) of material that is distinct from said weldable thermoplastic material is an outside layer made from a thermoplastic material.

10. A bag according to claim 9, characterized in that said weldable thermoplastic material is polyethylene (PE) and said thermoplastic material of the outside layer (PE) is polyester (PET).

11. A bag according to claim 1, characterized in that said layer (35) of weldable thermoplastic material has a thickness comprised between 20 μm and 110 μm.

12. A system for packaging diluted animal semen in bags, suitable for artificial insemination, in particular for porcine species, comprising a dilution extender of fresh semen (51) to give diluted semen (56) and bags to fill with said diluted semen; characterized in that said bags (10) are according to claim 1 and said dilution extender (53) is without antibiotic.

* * * * *